United States Patent
Ishizumi et al.

(10) Patent No.: US 9,304,083 B2
(45) Date of Patent: Apr. 5, 2016

(54) OPTICAL DETECTION DEVICE AND IMAGE FORMING APPARATUS INCLUDING THE SAME

(71) Applicant: CANON KABUSHIKI KAISHA, Tokyo (JP)

(72) Inventors: Keisuke Ishizumi, Hiratsuka (JP); Shinsuke Kobayashi, Yokohama (JP); Takeo Kawanami, Fujisawa (JP); Akinori Mitsumata, Tokyo (JP); Ken Nakagawa, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/606,419

(22) Filed: Jan. 27, 2015

(65) Prior Publication Data

US 2015/0211992 A1    Jul. 30, 2015

(30) Foreign Application Priority Data

Jan. 29, 2014  (JP) ................................ 2014-014192

(51) Int. Cl.
G03G 15/00    (2006.01)
G01N 21/55    (2014.01)
G01N 21/47    (2006.01)

(52) U.S. Cl.
CPC .............. *G01N 21/55* (2013.01); *G01N 21/474* (2013.01); *G03G 15/5058* (2013.01); *G01N 2021/556* (2013.01)

(58) Field of Classification Search
CPC .......... G03G 15/5041; G03G 15/5058; G03G 2215/00037; G03G 2215/00042; G03G 2215/0158; G03G 2215/0161

USPC ............................................... 399/49, 74, 301
See application file for complete search history.

(56) References Cited

U.S. PATENT DOCUMENTS

| 8,095,025 B2 * | 1/2012 | Ishibashi et al. ... G03G 15/5058 399/49 |
| 8,942,586 B2 * | 1/2015 | Tanaka et al. ...... G03G 15/5058 399/49 |

FOREIGN PATENT DOCUMENTS

| JP | 2006-208266 A | 8/2006 |
| JP | 2006-267644 A | 10/2006 |
| JP | 2013-191835 A | 9/2013 |

* cited by examiner

*Primary Examiner* — William J Royer
(74) *Attorney, Agent, or Firm* — Canon U.S.A., Inc. IP Division

(57) ABSTRACT

An optical detection device includes a light emitting element, a light receiving element, a housing including a first aperture and a second aperture, wherein light emitted from the light emitting element reaches the light receiving element through the second aperture after passing through the first aperture and being reflected by an irradiated surface, and a slope provided in the housing and inclined in an array direction of the light emitting element and the light receiving element, as viewed in a normal direction of the irradiated surface, wherein the slope is provided at a portion on an upstream side of the first aperture in an emission direction of light from the light emitting element, the portion faces the light emitting element in the array direction, and light emitted from the light emitting element enters the portion.

24 Claims, 18 Drawing Sheets

TRAVELING DIRECTION

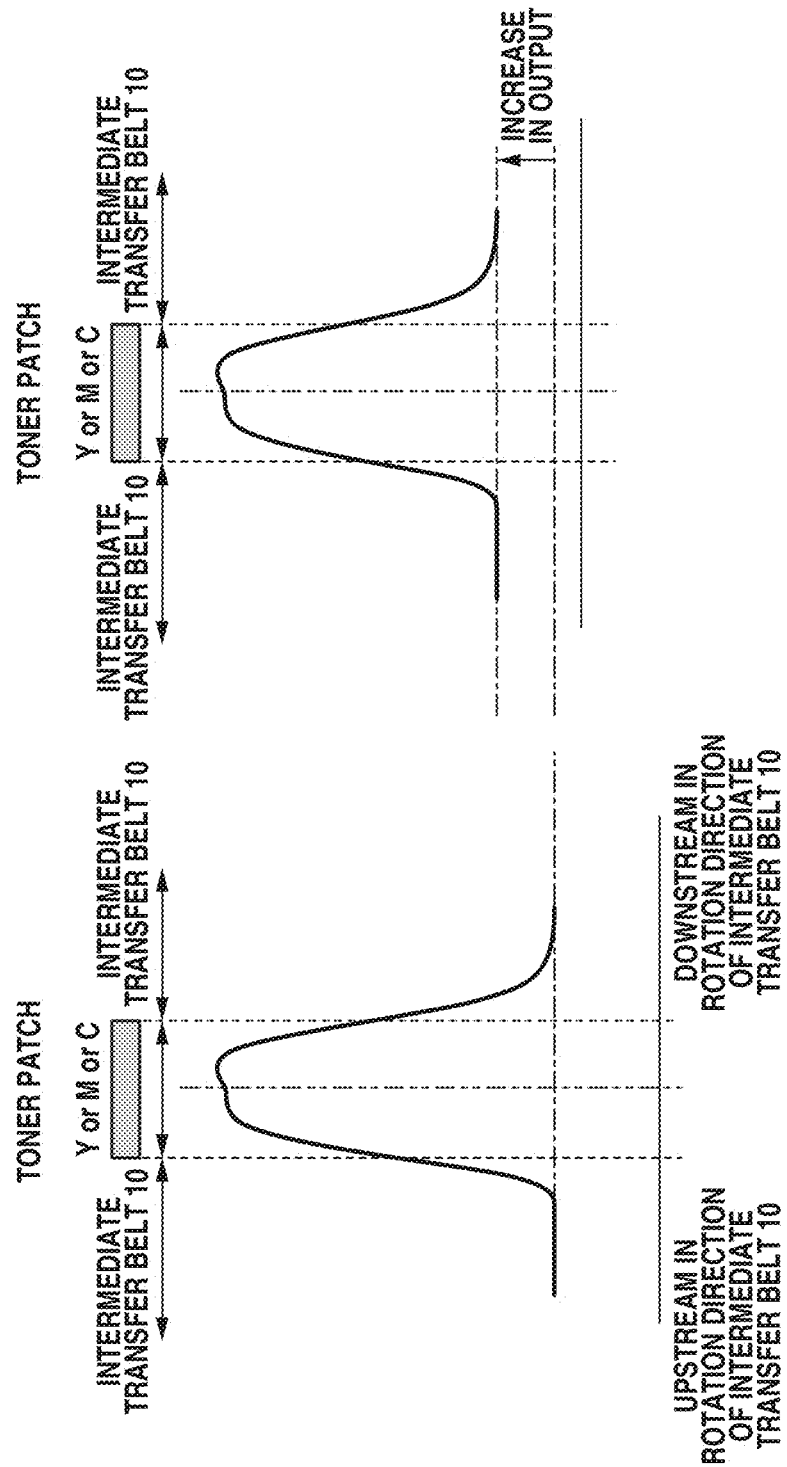

OPTICAL DETECTION DEVICE AND IMAGE FORMING APPARATUS INCLUDING THE SAME

BACKGROUND OF THE INVENTION

1. Field of the Invention

The present invention relates to an image forming apparatus, such as a laser beam printer (LBP) and a copier, in which an electrophotographic process and the like are used.

2. Description of the Related Art

With recent advances in computer network technologies, printers serving as image output terminals have rapidly become widespread. In recent years, as the color image output has been developed, there has been an increasing demand for improved stability of the image quality of color printers and for greater uniformity of the color image quality among different color printers.

In particular, there has been a demand for higher stability in the reproducibility of colors and in the accuracy of superimposing colors, irrespective of a change in an installation environment, a secular change, or a machine difference. With an electrophotographic image forming apparatus, however, image density or color registration varies due to a change in an environmental condition in which the image forming apparatus is placed, a deterioration of a photosensitive member or a developer over time, or a change in the temperature inside the image forming apparatus, and thus it is difficult to meet such a high demand without modifying the initial settings.

Thus, an optical sensor is typically used as a toner detection device that carries out feedback control for maintaining the image density and the color registration in optimum states. Such feedback control is carried out in the following manner. A test toner image (hereinafter, referred to as a "test pattern") is formed on a circulatory moving body, such as a photosensitive member, an intermediate transfer member, and a transfer conveyance belt, and the density of the test pattern and relative positions of the colors are measured by the optical sensor serving as the toner detection device.

Based on the measurement result and the conditions under which the test pattern has been formed, the image density and the color registration are then controlled so that the image density and the color registration would be optimized in actual printing. Parameters to be controlled include, for example, an exposure pattern in forming a latent image, an exposure start position, an image forming magnification, a developing bias, a charging bias, and the like.

As such an optical sensor serving as a toner detection device (toner detection sensor), a sensor that radiates light onto a test pattern and optically measures a toner amount or the position of a toner image based on the reflected light is often used.

Japanese Patent Application Laid-Open No. 2006-267644 discusses an optical sensor that includes, as optical elements, a light emitting element (light emitting diode (LED)) that radiates light onto an irradiated surface of a measurement target, a light receiving element for receiving specular reflection light, and a light receiving element for receiving diffuse reflection light. Each of the light emitting element and the light receiving elements is a so-called shell-type optical element, and is provided with a semiconductor chip including a light emitting portion or a light receiving portion, a shell-type lens unit, and a lead frame to be connected to a circuit board. With such a shell-type optical element, the orientation of the optical element can be modified freely to a certain degree by changing the angle at which the lead frame is bent. Therefore, each of the optical elements can be oriented in a desired direction by fitting each of the optical elements into a housing. However, a shell-type optical element may include a lens unit or a lead frame that is long to a certain degree so that the orientation of an element can be changed, and thus a certain volume is required between the semiconductor chip and the circuit board, which leads to a disadvantage in terms of downsizing the sensor.

In the meantime, in order to downsize a sensor, Japanese Patent Application Laid-Open No. 2006-208266 discusses an optical sensor in which an optical element, which is a chip component to be mounted on the surface of a circuit board, is used and the circuit board is covered by a housing provided with a light guide path. When an optical element that is to be mounted directly on the surface (mounting surface) of a circuit board is used, a lead frame and a lens unit are not provided, and thus the volume necessary for mounting the optical element directly on the circuit board is greatly reduced, enabling downsizing of the sensor. Typically, a chip-type light emitting element does not include a lens unit that is integrally formed with a light emitting portion as in a shell-type light emitting element, and thus has a large directional angle light emission. Therefore, with the configuration discussed in Japanese Patent Application Laid-Open No. 2006-208266, light from the light emitting element is condensed by using a condensing lens, and an irradiated surface is irradiated with the condensed light. However, with an optical sensor in which a chip-type optical element is mounted on the surface of a circuit board as discussed in Japanese Patent Application Laid-Open No. 2006-208266, a variation is likely to occur in a position at which a light emitting element is mounted on the surface of the circuit board. Therefore, in a case in which the position of the light emitting element is not aligned with the optical axis of the condensing lens, an irradiation position on the irradiated surface is likely to vary, and light having desired light amount cannot be radiated at a desired position on the irradiated surface. Therefore, the amount of light received by a light receiving element decreases, and the detection accuracy may be degraded.

Thus, Japanese Patent Application Laid-Open No. 2013-191835 discusses a configuration in which, without using a lens, an irradiated surface is irradiated with light from a light emitting element through an aperture provided in a housing that covers the light emitting element. According to this configuration, even if a variation occurs in the position at which the light emitting element is mounted, an irradiation position on the irradiated surface is less likely to vary.

However, with the configuration in which light is radiated from the light emitting element through the aperture, stray light may be generated depending on the shape of the housing. In other words, for example, some of the light emitted from the light emitting element is reflected inside the housing prior to being emitted through the aperture, and passes through the aperture in a direction that is different from an originally intended direction. Thus, the light is radiated onto the irradiated surface at a position different from a desired position and specularly-reflected, and the reflected light reaches, as stray light, the light receiving element that receives diffuse reflection light. In such a case, the stray light may change the amount of light received by the light receiving element that receives diffuse reflection light, and a correct output may not be obtained from the light receiving element. Consequently, the accuracy in detecting the irradiated surface by using an optical detection device may be degraded.

SUMMARY OF THE INVENTION

The present invention is directed to an optical detection device that can suppress occurrence of stray light and can obtain a highly precise output.

According to an aspect of the present invention, an optical detection device includes a light emitting element being positioned by being mounted on a substrate, a light receiving element, a housing including a first aperture through which light emitted from the light emitting element passes and a second aperture which is different from the first aperture and through which light to be received by the light receiving element passes, and enclosing the light emitting element and the light receiving element, wherein light emitted from the light emitting element reaches the light receiving element through the second aperture after passing through the first aperture and being reflected by an irradiated surface, and a slope provided in the housing and inclined in an array direction of the light emitting element and the light receiving element, as viewed in a normal direction of the irradiated surface, wherein the slope is provided at a portion on an upstream side of the first aperture in an emission direction of light from the light emitting element, the portion faces the light emitting element in the array direction, and light emitted from the light emitting element enters the portion.

According to another aspect of the present invention, an image forming apparatus for forming an image on a recording material by transferring a toner image onto the recording material, include: an image forming unit configured to form a toner image on an image bearing member; an optical detection device including a light emitting element being positioned by being mounted on a substrate, a light receiving element, a housing including a first aperture through which light emitted from the light emitting element passes and a second aperture which is different from the first aperture and through which light to be received by the light receiving element passes, and enclosing the light emitting element and the light receiving element, wherein light emitted from the light emitting element reaches the light receiving element through the second aperture after passing through the first aperture and being reflected by an irradiated surface of the image bearing member, and a slope provided in the housing and inclined in an array direction of the light emitting element and the light receiving element, as viewed in a normal direction of the irradiated surface, wherein the slope is provided at a portion on an upstream side of the first aperture in an emission direction of light from the light emitting element, the portion faces the light emitting element in the array direction, and light emitted from the light emitting element enters the portion; and a control unit configured to control an image forming condition of the image forming unit based on an output from the optical detection device.

Further features of the present invention will become apparent from the following description of exemplary embodiments with reference to the attached drawings.

BRIEF DESCRIPTION OF THE DRAWINGS

FIGS. 13A and 13B are diagrams for comparing a detection waveform obtained through a configuration of the first exemplary embodiment and a detection waveform obtained through a configuration of the comparative example.

DESCRIPTION OF THE EMBODIMENTS

Hereinafter, exemplary embodiments of an image forming apparatus including an optical sensor according to the present invention will be described in detail.

[Image Forming Apparatus]

Figure 1:
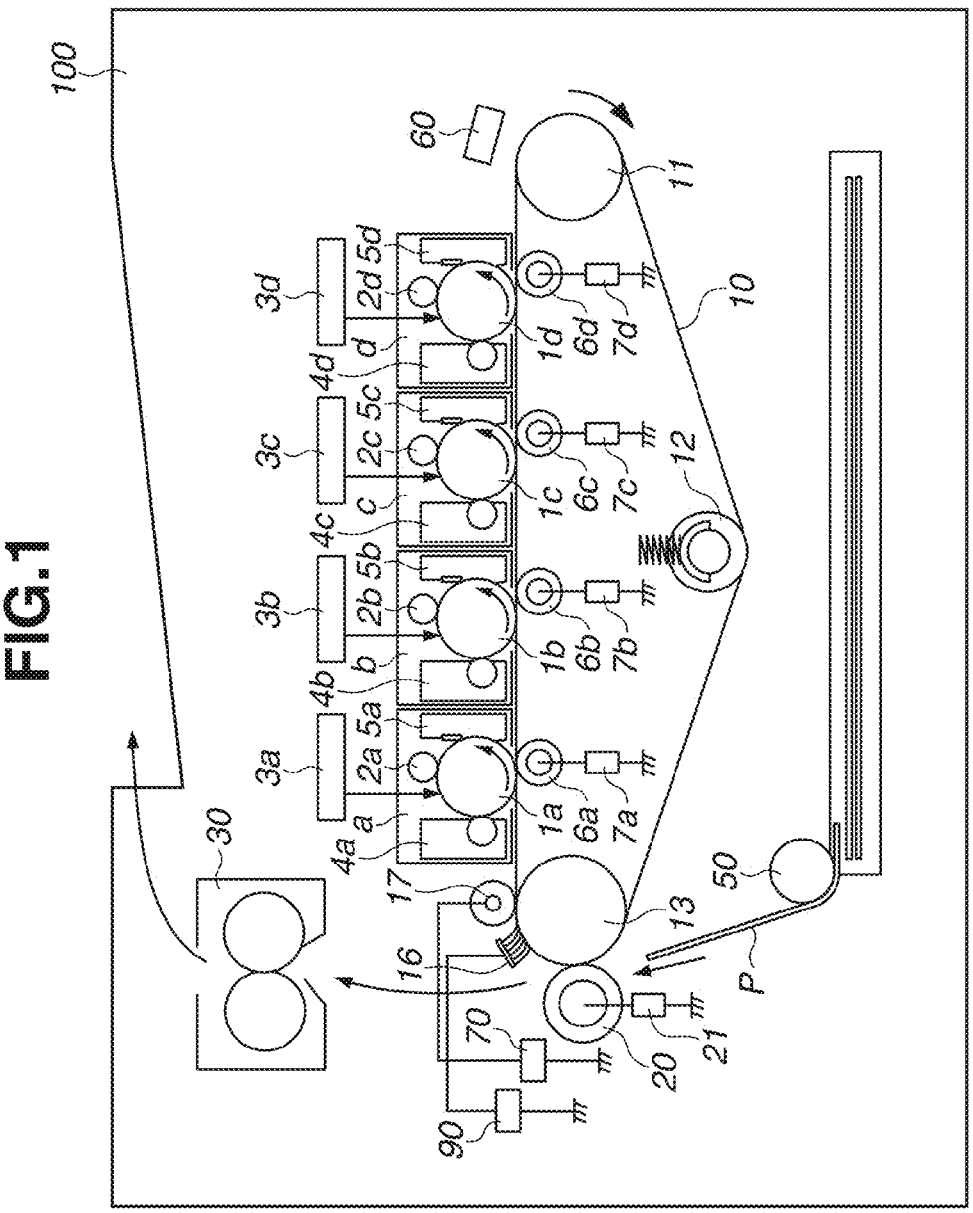
FIG. 1 schematically illustrates a configuration of an image forming apparatus according to a first exemplary embodiment.

First, an image forming apparatus 100 will be described. FIG. 1 schematically illustrates a configuration of the image forming apparatus 100. The image forming apparatus 100 includes first through fourth image forming stations a through d. The first through fourth image forming stations a through d form toner images of mutually different colors, and the image forming apparatus 100 can form a color image by combining the toner images. The first image forming station a forms a yellow toner image, the second image forming station b forms a magenta toner image, the third image forming station c forms a cyan toner image, and the fourth image forming station d forms a black toner image. The first through fourth image forming stations a through d include respective photosensitive drums 1 (1a, 1b, 1c, 1d) serving as first image bearing members, and the photosensitive drums 1 are rotationally-driven in directions indicated by respective arrows by a motor (not illustrated) in such a manner that each photosensitive drum 1 rotates at a surface speed of 100 mm/sec with the diameter of the photosensitive drum 1 being the center value. Toner images on the respective photosensitive drums 1 of the first through fourth image forming stations a through d are sequentially primary-transferred onto an intermediate transfer belt 10 serving as a second image bearing member. In this manner, the image forming apparatus 100 is a so-called inline printer.

Hereinafter, an image forming operation by the image forming apparatus 100 will be described. It is to be noted that the operations of the first through fourth image forming stations a through d are similar to one another; therefore, the image forming operation of the first image forming station a will be described, and the descriptions of the operations of the second through fourth image forming operations b through d will be omitted. The photosensitive drum 1a is charged uniformly to a predetermined potential by a charging roller 2a. An exposure unit 3a then radiates a laser beam. Hereinafter, a scanning direction in which a spot of a laser beam moves on the surface of the photosensitive drum 1a is referred to as a main scanning direction, and on the surface of the photosensitive drum 1a, a direction that is orthogonal to the main scanning direction is referred to as a sub-scanning direction. The main scanning direction is parallel to a rotation axis direction of the photosensitive drum 1a. Through the operation described above, an electrostatic latent image corresponding to a yellow color in a color image is formed. Thereafter, the electrostatic latent image is developed by a first developing device (yellow developing device) 4a at a developing position, and a yellow toner image is thus visualized.

Regarding an irradiation direction of a laser beam, the photosensitive drums 1a and 1b for yellow and magenta are each scanned by a laser beam in a left-to-right direction and the photosensitive drums 1c and 1d for cyan and black are each scanned by a laser beam in a right-to-left direction, when facing the front of an image on a recording medium. The yellow toner image formed on the photosensitive drum 1a is transferred onto the intermediate transfer belt 10, which can bear a toner image, when passing through a primary transfer portion which is an abutment portion of the photosensitive drum 1a and the intermediate transfer belt 10 (a primary transfer process). This primary transfer process is carried out by a primary transfer high voltage power supply 7a applying a primary transfer voltage to a primary transfer roller 6a. Primary-transfer residual toner remaining on the photosensitive drum 1a is cleaned by a cleaning device 5a. If printing is to be continued, the operation returns to the image forming process of charging and thereafter. Thereafter, in a similar manner, a magenta toner image of a second color, a cyan toner image of a third color, a black toner image of a fourth color are formed, and the toner images are sequentially transferred onto the intermediate transfer belt 10 so as to be superimposed on one other, and thus a color toner image is obtained. The color toner images of the four colors on the intermediate transfer belt 10 are collectively transferred onto a surface of a recording material P fed by a sheet feeding unit 50 when passing through a secondary transfer portion which is an abutment portion of the intermediate transfer belt 10 and a secondary transfer roller 20 (a secondary transfer process). This secondary transfer process is carried out by a secondary transfer high voltage power supply 21 applying a secondary transfer voltage to the secondary transfer roller 20. Thereafter, the recording material P bearing the toner images of the four colors is conveyed to a fixing device 30 and is heated and pressed in the fixing device 30, and thus the toner of the four colors is molten and mixed and is thus fixed onto the recording material P. Through the operation described above, a full color image is formed.

Meanwhile, secondary-transfer residual toner which is a mixture of positive polarity toner and negative polarity toner is present on the intermediate transfer belt 10 that has undergone the secondary transfer process. The secondary-transfer residual toner is scattered uniformly and charged by a conductive brush 16. A voltage of positive polarity is applied to the conductive brush 16 by a conductive brush high voltage power supply 90, and thus the secondary-transfer residual toner is positively charged. In addition, a voltage of positive polarity is applied to a conductive roller 17 by a conductive roller high voltage power supply 70, and thus the secondary-transfer residual toner is further charged positively. The secondary-transfer residual toner that has been positively charged is transferred onto the photosensitive drums 1 in the primary transfer portion, and is collected into the cleaning devices 5 (5a, 5b, 5c, 5d) disposed on the photosensitive drums 1. In addition, two optical sensors 60 are disposed facing a drive roller 11, and the optical sensors 60 are spaced apart from each other in the main scanning direction of the laser beam. Each of the optical sensors 60 includes a light emitting element that emits infrared light, a light receiving element that mainly receives diffuse reflection light, and a light receiving element that mainly receives specular reflection light. By detecting, via the optical sensors 60, a test pattern formed on the intermediate transfer belt 10 at a timing that is different from that in the normal printing period, registration correction for correcting a relative misregistration amount among different colors, or density correction is carried out.

[Intermediate Transfer Belt]

Subsequently, the intermediate transfer belt 10 will be described. The center value of the circumference of the intermediate transfer belt 10 is 650 mm. The intermediate transfer belt 10 is stretched around three axes at the drive roller 11, a tension roller 12, and a secondary transfer counter roller 13, and is rotationally-driven by rotating the drive roller 11 via the same motor as the motor for rotationally-driving the photosensitive drums 1. The intermediate transfer belt 10 is set to rotate at a surface speed of 100 mm/sec when the diameter of the drive roller 11 is the center value, but the surface speed varies due to a manufacturing variation in the outer diameter of the drive roller 11. In addition, the intermediate transfer belt 10 having a surface glossiness of 30 or higher (the glossiness is measured by using a gloss meter called the Gloss Checker IG-320 manufactured by Horiba, Ltd.) is used so that infrared light radiated from the optical sensors 60 is specularly-reflected on the surface of the intermediate transfer belt 10.

[Description of Control Block Diagram]

Figure 2:
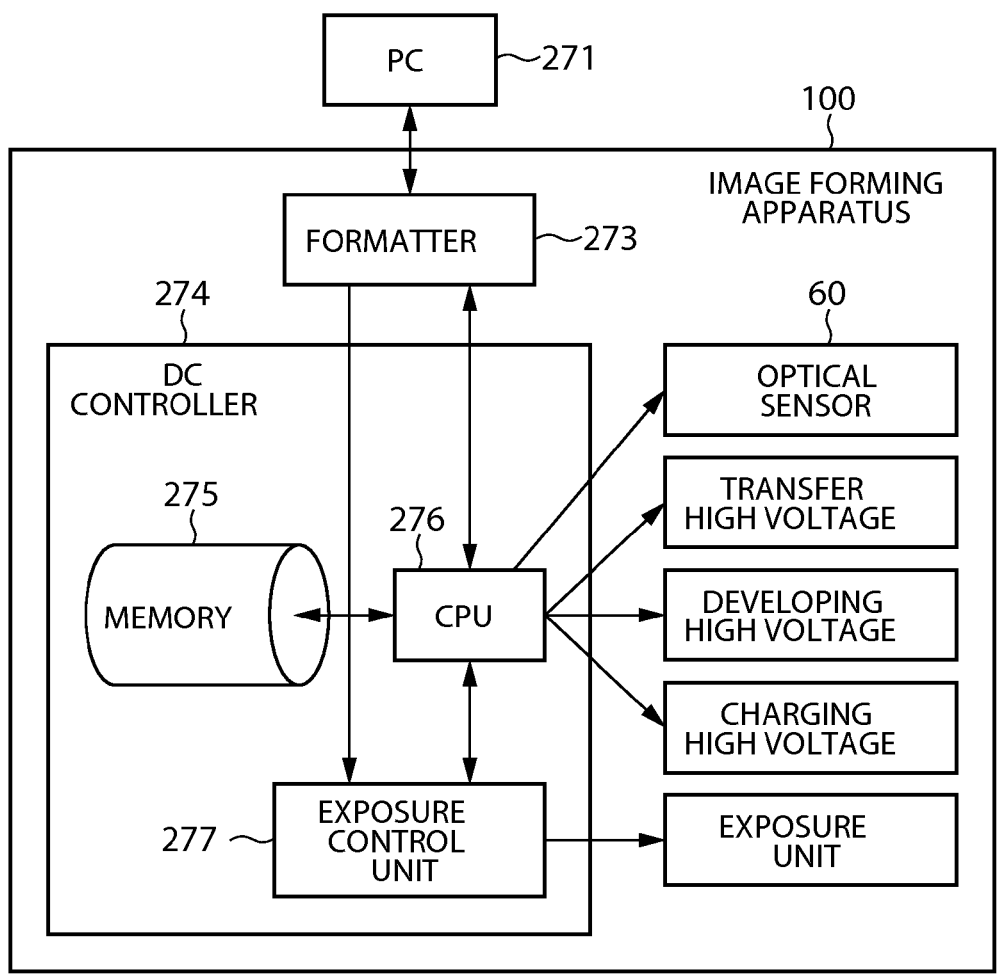
FIG. 2 illustrates a control block for controlling an operation of the image forming apparatus.

Subsequently, a control block will be described. FIG. 2 illustrates a control block for controlling the operation of the image forming apparatus 100. A personal computer (PC) 271 serving as a host computer issues a print instruction to a formatter 273 provided inside the image forming apparatus 100, and transmits image data of an image to be printed to the formatter 273. The formatter 273 converts the image data received from the PC 271 into exposure data and transfers the exposure data to an exposure control unit 277 provided inside a direct current (DC) controller 274. The exposure control unit 277 controls an exposure unit by controlling on/off of the exposure data, in accordance with an instruction from a central processing unit (CPU) 276. The CPU 276 starts an image forming sequence, upon receiving a print instruction from the formatter 273. The DC controller 274 is provided with the CPU 276, a memory 275, and the like, and carries out a preprogrammed operation. The CPU 276 forms an electrostatic latent image by controlling a charging high voltage, a developing high voltage, and a transfer high voltage, or forms an image by controlling a transfer or the like of a developed toner image.

In addition, the CPU 276 carries out processing of receiving a signal from the optical sensors 60 in calibration. In calibration, the amount of reflection light from the surface of the intermediate transfer belt 10 or from a test patch formed on the intermediate transfer belt 10 is measured. The CPU 276 detects an optical signal from a test patch received by the light receiving element of the optical sensors 60, and rising and falling edges of the optical signal, and the detected signal is stored in the memory 275. After the calibration is finished, the CPU 276 carries out calculation and makes setting of various image forming conditions. The optical sensors 60 are not operated in a normal printing sequence but are operated at the time of calibration such as registration correction control, density control, and the like.

[Optical Sensor]

The image forming apparatus 100 includes the optical sensors (optical detection device) 60 for carrying out the registration correction control and the density control. The optical sensors 60 detect a test pattern formed by toner patches that are formed on the surface of the intermediate transfer belt 10 by using the first through fourth image forming stations a through d described above.

Figure 8:
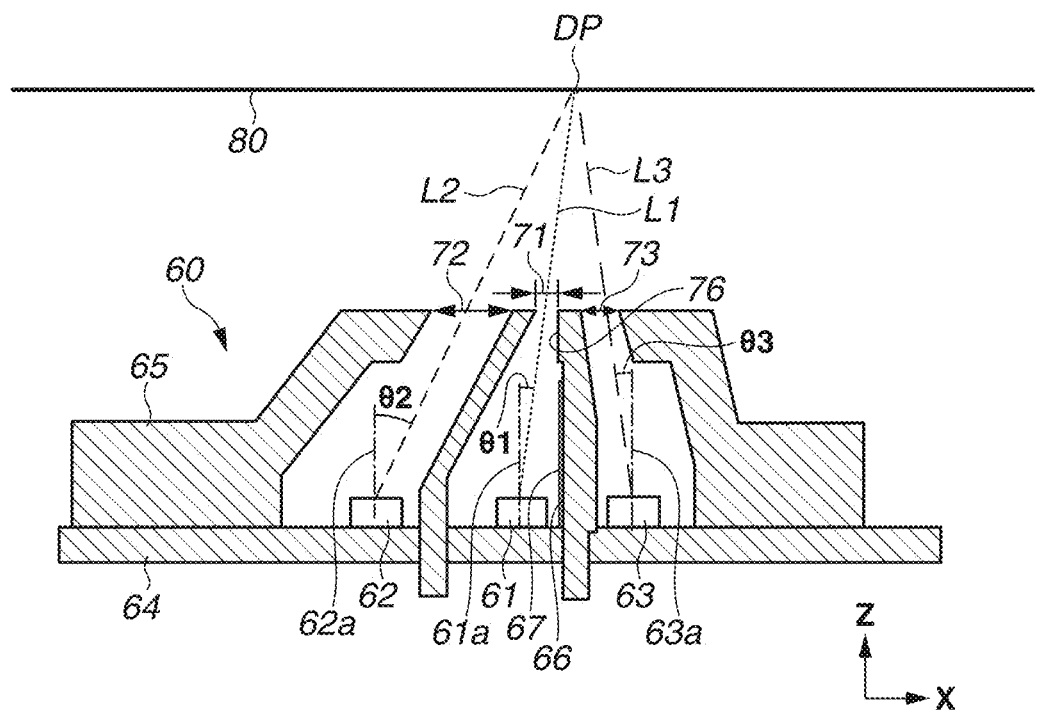
FIG. 8 is a sectional view of an optical sensor according to the first exemplary embodiment.

The configuration of the optical sensors 60 will now be described. FIG. 8 is a sectional view of the optical sensors 60 as viewed in a direction parallel to the surface of an irradiated surface 80. An X direction is a direction parallel to the main scanning direction, and a Z direction is a direction orthogonal to the main scanning direction. The irradiated surface 80 corresponds to the surface of the intermediate transfer belt 10. The optical sensors 60 include a chip-type light emitting element 61 and chip-type light receiving elements 62 and 63, which are mounted directly on a substrate 64. The light receiving element 62 is a light receiving element for receiving diffuse reflection light, and the light receiving element 63 is a light receiving element for receiving specular reflection light. A housing 65 is disposed on the substrate 64 so as to cover the light emitting element 61 and the light receiving elements 62 and 63, and thus the light emitting element 61 and the light receiving elements 62 and 63 are enclosed in respective spaces defined by the housing 65 and the substrate 64 (spaces inside the housing 65). Light guide paths (apertures) respectively corresponding to the light emitting element 61 and the light receiving elements 62 and 63 are formed in the housing 65. A light emitting aperture (first aperture) 71 corresponding to the light emitting element 61 has a diameter of 0.8mm, a light receiving aperture (second aperture) 72 corresponding to the light receiving element 62 has a diameter of 2.5 mm, and a light receiving aperture (third aperture) 73 corresponding to the light receiving element 63 has a diameter of 1.0 mm. In a first exemplary embodiment, an infrared light emitting diode SEC1G01C manufactured by Sanken Electric Co., Ltd. is used as the light emitting element 61, but other light emitting elements may instead be used. In addition, phototransistors SML-810TB manufactured by ROHM Co., Ltd. are used as the light receiving elements 62 and 63, but other light receiving elements may instead be used as well. In the present exemplary embodiment, the optical sensor 60 is disposed in such a manner that the light emitting element 61 and the light receiving elements 62 and 63 are aligned along a straight line parallel to the main scanning direction of the laser beam. In other words, in the main scanning direction, the surface of the irradiated surface 80 is parallel to the surface of the substrate 64.

In addition, since each of the light emitting element 61 and the light receiving elements 62 and 63 is of a chip type, their positions held when being mounted on the substrate 64 are determined by the surface of the substrate 64, or by a circuit unit, a solder unit, and the like provided on the surface of the substrate 64. In the present exemplary embodiment, the light emitting element 61 and the light receiving elements 62 and 63 are positioned in such a manner that respective central optical axes 61a, 62a, and 63a thereof are perpendicular to the surface of the substrate 64. In addition, the central axes 61a, 62a, and 63a are parallel to the normal of the irradiated surface 80 at a detecting position DP.

Subsequently, the optical axes will be described. An axis L1 connecting the center (light emitting point) of the light emitting element 61 and the detecting position DP on the irradiated surface 80 is defined as the central optical axis of the irradiation light. An axis L2 connecting the center (light receiving point) of the light receiving element 62 and the detecting position DP is defined as the central optical axis of the diffuse reflection light. An axis L3 connecting the center (light receiving point) of the light receiving element 63 and the detecting position DP is defined as the central optical axis of the specular reflection light. The directions of these central optical axes L1, L2, and L3 are determined in accordance with the shapes of the respective apertures (the light emitting aperture 71, the light receiving aperture 72, and the light receiving aperture 73) corresponding to the light emitting element 61 and the light receiving elements 62 and 63, respectively, and the central optical axes L1, L2, and L3 are set so as to intersect with one another at the detecting position DP on the irradiated surface 80. In addition, light emitted from the light emitting element 61 is radiated onto the irradiated surface 80 without passing through a condensing member such as a lens, and light reflected by the irradiated surface 80 reaches the light receiving elements 62 and 63 without passing through a condensing member such as a lens.

An angle $\theta 1$ formed between the central optical axis L1 and the normal direction of the surface of the irradiated surface 80 at the detecting position DP is 15°. By setting an angle $\theta 3$ formed between the central optical axis L3 and the normal direction of the surface of the irradiated surface 80 at the detecting position DP at 15° as well, light specularly-reflected at the detection detecting position DP on the irradiated surface 80 enters the light receiving element 63. In addition, by setting an angle $\theta 2$ formed between the central optical axis L2 and the normal direction of the surface of the irradiated surface 80 at the detecting position DP at 35°, light diffuse-reflected at the detection position DP on the irradiate target face 80 mainly enters the light receiving element 62. In a case in which a yellow, magenta, or cyan toner patch is present at a position on the intermediate transfer belt 10 serving as the irradiated surface 80 that is a position corresponding to the detecting position DP, the irradiation light from the light emitting element 61 is mainly diffuse-reflected, and some of the diffuse reflection light is received by the light receiving element 62. In addition, in a case in which a toner patch is not present at a position on the intermediate transfer belt 10 that corresponds to the detecting position DP, the irradiation light from the light emitting element 61 is mainly specularly-reflected, and the specular reflection light is received by the light receiving element 63.

Subsequently, directional characteristics of the light emission intensity of the light emitting element 61 will be described. While the light emitting element 61 radiates divergent infrared light, the intensity of the irradiation light is not uniform. The irradiation intensity differs even when the distance from the light emitting element 61 is the same if the angle at which the infrared light is emitted from the light emitting element 61 differs. This is referred to as the directional characteristics of the light emission intensity.

Figure 9:
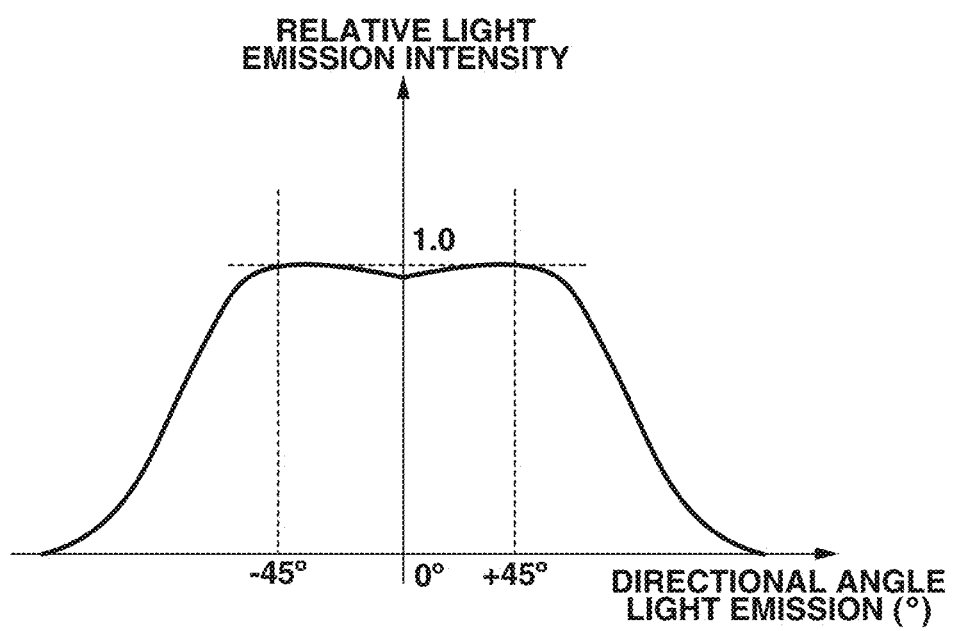
FIG. 9 illustrates a directional angle characteristic of a light emitting element.

FIG. 9 illustrates the directional characteristics of the light emission intensity of the light emitting element 61. The central axis 61a coincides with the directional angle light emission of 0°. The light emission intensity stays substantially constant in a range from 0° to ±45°, and the light emission intensity decreases rapidly as the angle exceeds ±45° in both positive and negative directions. In this manner, the light emitting element 61 has relatively broad directional characteristics of the light emission intensity. Therefore, even if the positional relationship between the light emitting element 61 and the light emitting aperture 71 deviates to a certain degree from a nominal positional relationship due to a variation in the mounting position held when the light emitting element 61 is mounted on the substrate 64, infrared light at a sufficient intensity is emitted through the light emitting aperture 71.

Figure 10:
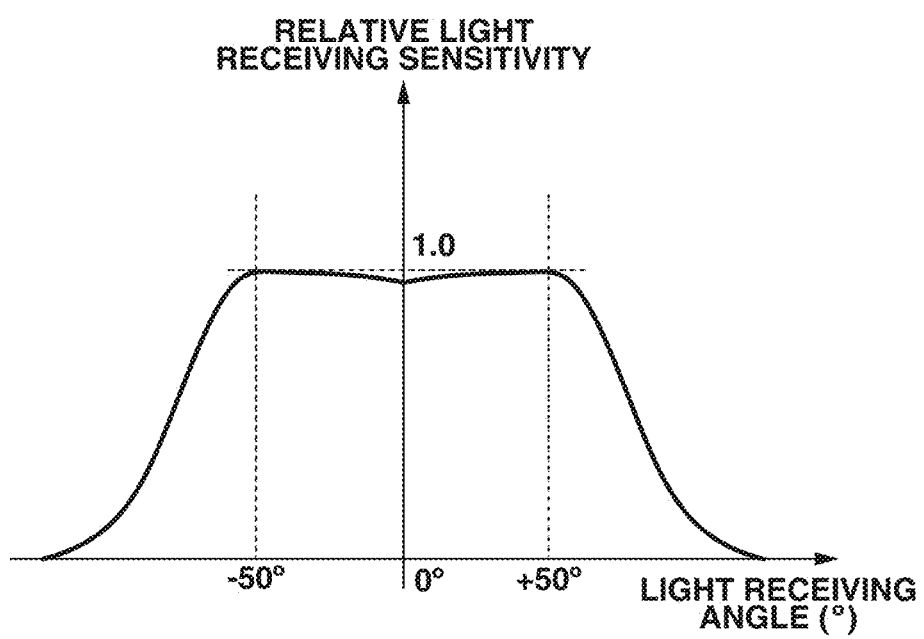
FIG. 10 illustrates a directional angle characteristic of light receiving elements.

Subsequently, directional characteristics of the light receiving sensitivity of the light receiving elements 62 and 63 will be described. The light receiving sensitivity of the light receiving elements 62 and 63 differs in accordance with the incident angle even if the distance from the light emitting element 61 is the same. This is referred to as the directional characteristics of the light receiving sensitivity. FIG. 10 illustrates the directional characteristics of the light receiving sensitivity of the light receiving elements 62 and 63. The central axes 62a and 63a coincide with the light receiving angle of 0°. The light receiving sensitivity stays substantially constant in a range from 0° to ±50°, and the light receiving sensitivity decreases rapidly as the angle exceeds ±50° in both positive and negative directions. As the light receiving elements 62 and 63 have broad directional angle characteristics of the light receiving sensitivity as described above, even when the angle θ2 of the light receiving element 62 is 35°, good light receiving sensitivity can be obtained. In other words, the light receiving elements 62 and 63 have the directional characteristics of the light receiving sensitivity in a relatively broad angle. Therefore, even if the positional relationships between the light receiving elements 62 and 63 and the respective light receiving apertures 72 and 73 deviate to a certain degree from a nominal positional relationship due to a variation in the mounting position held when the light receiving elements 62 and 63 are mounted on the substrate 64, the light receiving elements 62 and 63 can receive the incident light at sufficient sensitivity.

[Description of Circuit Configuration of Optical Sensor 60]

Figure 3:
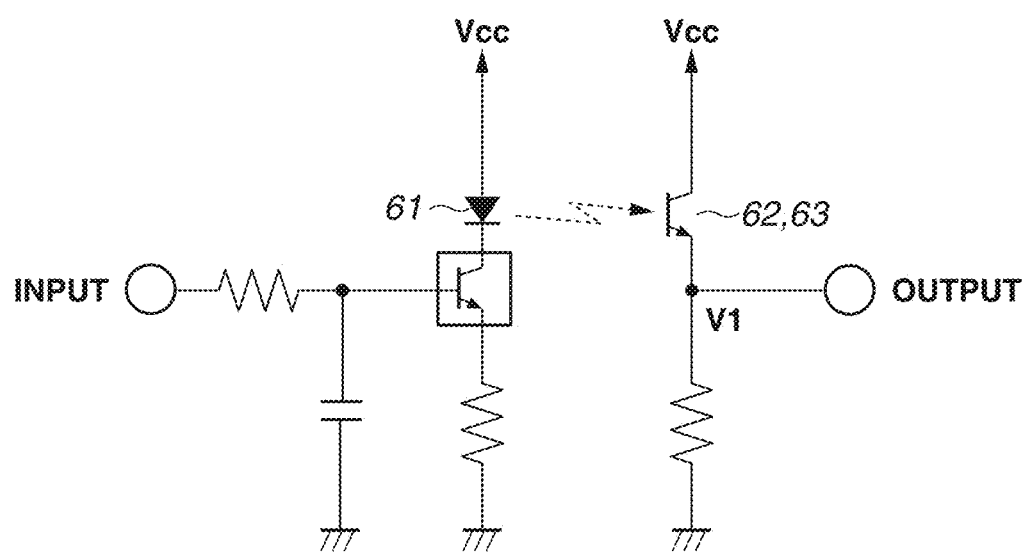
FIG. 3 illustrates a circuit configuration according to the first exemplary embodiment.

The circuit configuration of the optical sensor 60 will now be described. FIG. 3 illustrates an example of the circuit configuration of the optical sensor 60.

The light emitting element 61 radiates infrared light onto the irradiated surface 80 (intermediate transfer belt 10), and the light receiving elements 62 and 63 receive reflection light from the irradiated surface 80. Detection currents of the light receiving elements 62 and 63 are converted into V1 by an IV (current/voltage) conversion circuit, and V1 is input to an analog-to-digital (AD) conversion port of the CPU 276 provided in the DC controller 274 illustrated in FIG. 2. Thus, the analog voltage value is converted into digital data, which is then used in calculation.

In addition, an on/off operation and light amount adjustment of the light emitting element 61 are carried out by varying an LED driving current that is input to an input terminal illustrated in FIG. 3 through pulse width modulation (PWM) control of the CPU 276 provided in the DC controller 274.

[Description of Registration Correction Control]

Subsequently, the registration correction control will be described.

Figure 4:
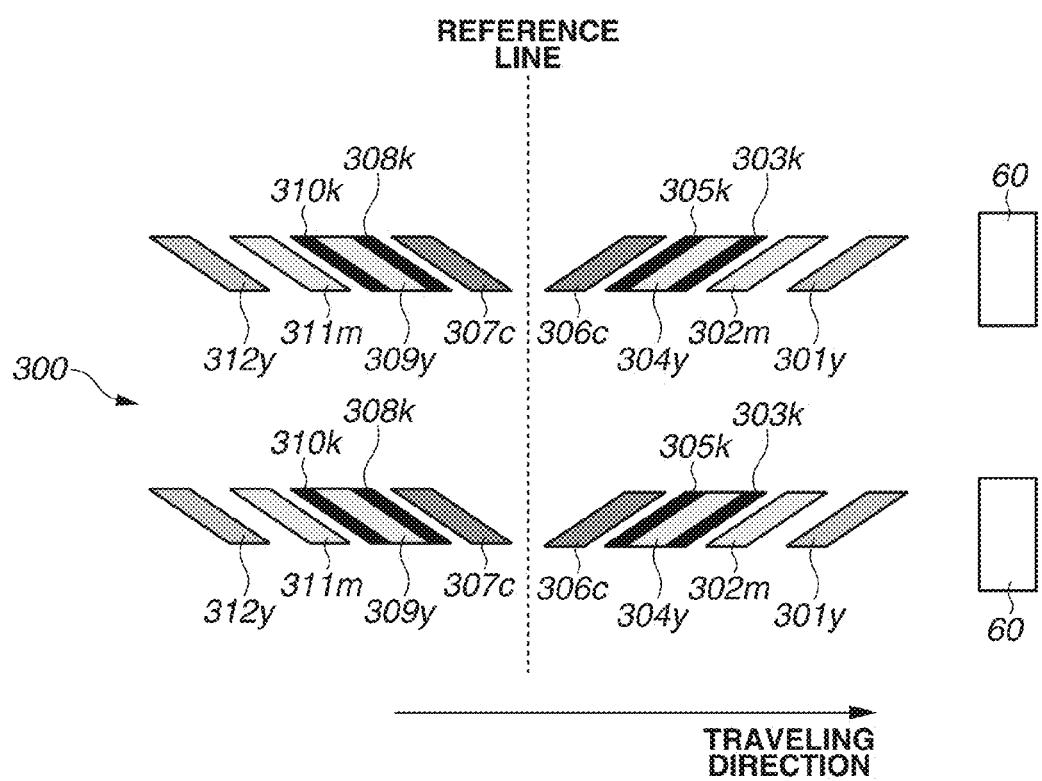
FIG. 4 illustrates a test pattern for registration correction.

FIG. 4 illustrates a test pattern for registration correction that is to be formed on the surface of the intermediate transfer belt 10. A test pattern 300 is a collection of parallelogram toner patches (toner images for detection) formed by toner of the respective colors of yellow (301y, 304y, 309y, 312y), magenta (302m, 311m), cyan (306c, 307c), and black (303k, 305k, 308k, 310k). Each of these toner patches are disposed at two positions that are spaced apart from each other in the main scanning direction so as to be symmetric with respect to a reference line, which passes through the middle of the intermediate transfer belt 10 in the main scanning direction and is orthogonal to the main scanning direction. The main scanning direction is parallel to the rotation axis direction of the drive roller 11. The optical sensors 60 are disposed so as to face the intermediate transfer belt 10, at the respective two positions that are spaced apart from each other in the main scanning direction so as to respectively correspond to the two test patterns 300 formed spaced apart from each other in the main scanning direction.

Figure 5A:
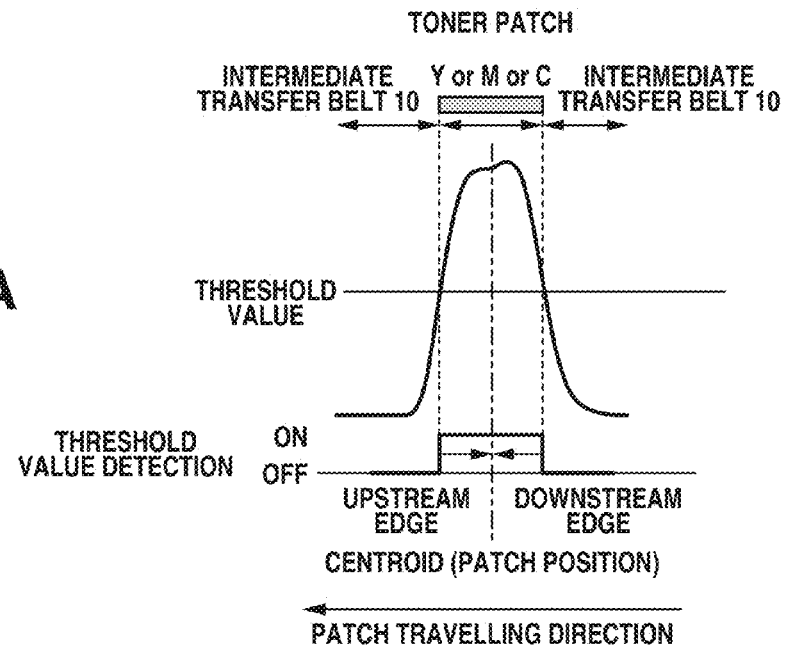
FIGS. 5A and 5B each illustrate a detection waveform obtained when diffuse reflection light from a test pattern is detected by a light receiving element.

The test pattern 300 is formed on the intermediate transfer belt 10 through the image forming operation described above, and the test pattern 300 on the intermediate transfer belt 10 is detected by the optical sensor 60, whereby the registration correction is carried out based on the detection result. When infrared light radiated from the light emitting element 61 is reflected by the surface of the intermediate transfer belt 10 where a toner image is not formed, most of the infrared light is specularly-reflected, and thus the reflection light from the intermediate transfer belt 10 is not detected by the light receiving element 62 that receives diffuse reflection light. In the meantime, when infrared light radiated from the light emitting element 61 is reflected by a portion of the intermediate transfer belt 10 where yellow, magenta, and cyan toner images of the test pattern 300 are formed, the reflection light is mainly diffuse reflection light. Therefore, the reflection light from the toner image portion can be detected by the light receiving element 62. FIG. 5A illustrates an output waveform (a detection waveform) of the light receiving element 62 obtained when yellow, magenta, and cyan toner patches of the test pattern 300 pass through a position facing the optical sensor 60 (detecting position DP) while the surface of the intermediate transfer belt 10 is moved. While the toner patches pass through the detecting position DP, the light emitting element 61 radiates infrared light onto the detecting position DP. The output waveform corresponds to the amount of received reflection light.

Figure 5B:
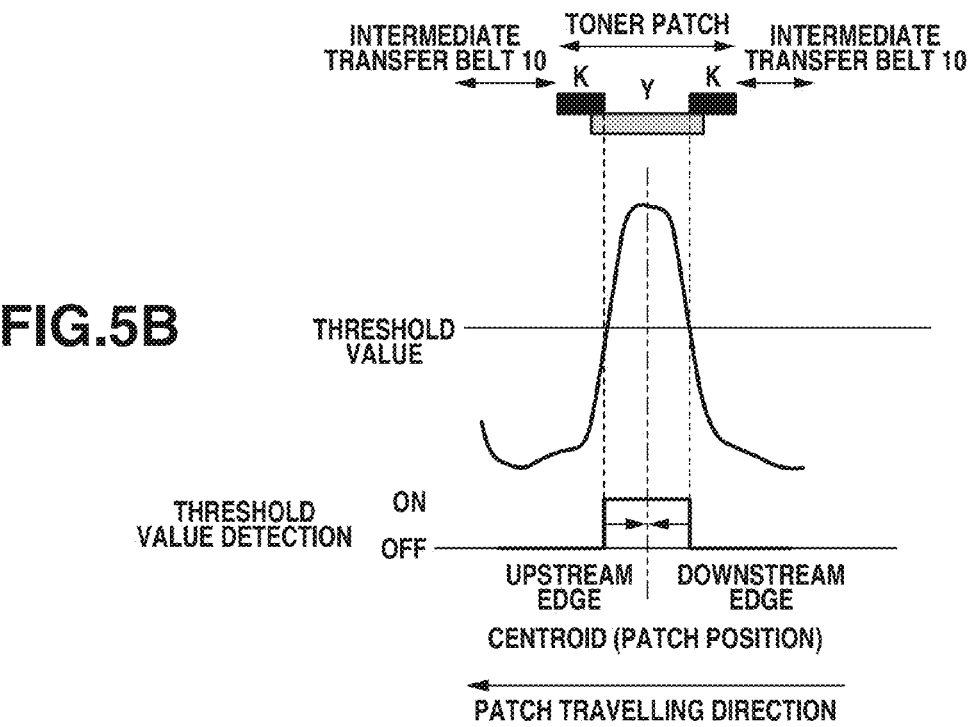

A timing at which the detection result of the test pattern 300 falls below or exceeds a preset threshold value is regarded as an edge of the toner patches. Specifically, a timing at which a detection output of a patch of the test pattern 300 exceeds the threshold value while rising is defined as an upstream edge of the patch. Meanwhile, a timing at which a detection output of a patch falls below the threshold value while falling is defined as a downstream edge of the patch. Then, a midpoint between the upstream and downstream edge timings is defined as the position of the patch. As the dynamic range, which is a difference between a detection output obtained when a toner patch is present in the detecting position DP and a detection output obtained when a toner patch is not present, is broader, the edges can be detected more stably without being affected by outside noise or the like. Meanwhile, black toner primarily absorbs infrared light, and thus it is difficult to identify the position of a black toner image by detecting diffuse reflection light. Therefore, as illustrated in FIG. 5B, black patches are formed so as to overlap a yellow patch at two ends of the yellow patch in the sub-scanning direction. Through this, by detecting diffuse reflection light from the yellow patch portion, timings at which the detection output falls below or exceeds the threshold value can be regarded as edges of the black patch, and thus the position of the black patch can be calculated from the edges.

The detection result of the intermediate transfer belt 10 or the test pattern 300 is output to the DC controller 274. The DC controller 274 detects a passing timing of the test pattern 300 based on the output from the optical sensor 60 and calculates the position. Then, by comparing the result with a predetermined timing, the DC controller 274 calculates a relative color misregistration amount among different colors in the main scanning direction and the sub-scanning direction, the magnification in the main scanning direction, relative inclination, and the like. According to the obtained result, the DC controller 274 sets (modifies) image forming conditions so that the relative color misregistration amount among the different colors is reduced. Specific image forming conditions to be corrected through the registration correction control include laser beam emission start timings of the exposure units 3.

[Description of Density Correction Control]

Figure 6:
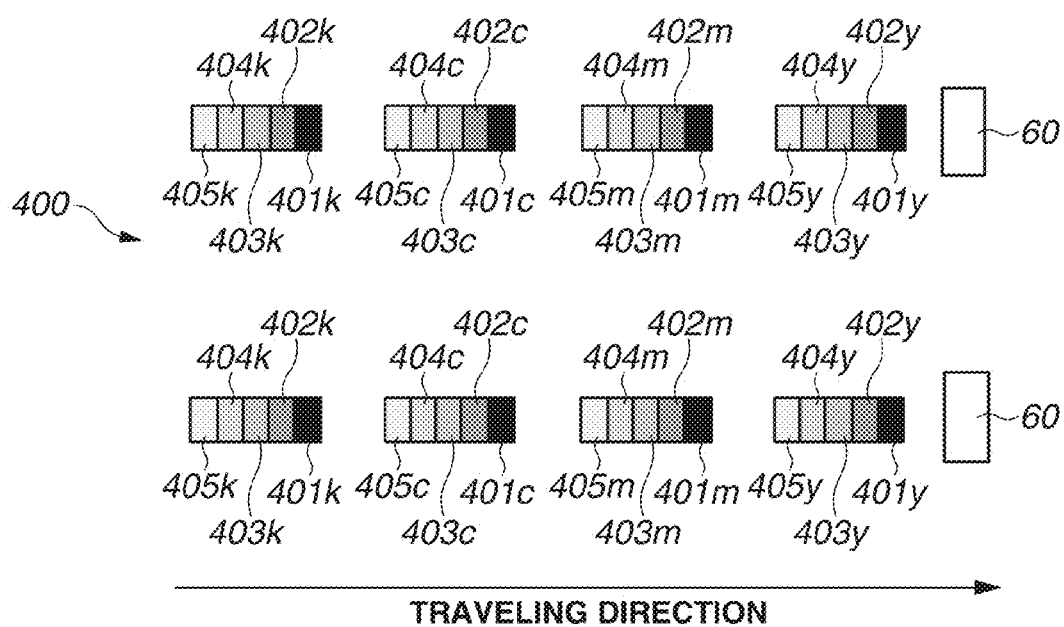
FIG. 6 illustrates a test pattern for density correction.
Figure 7:
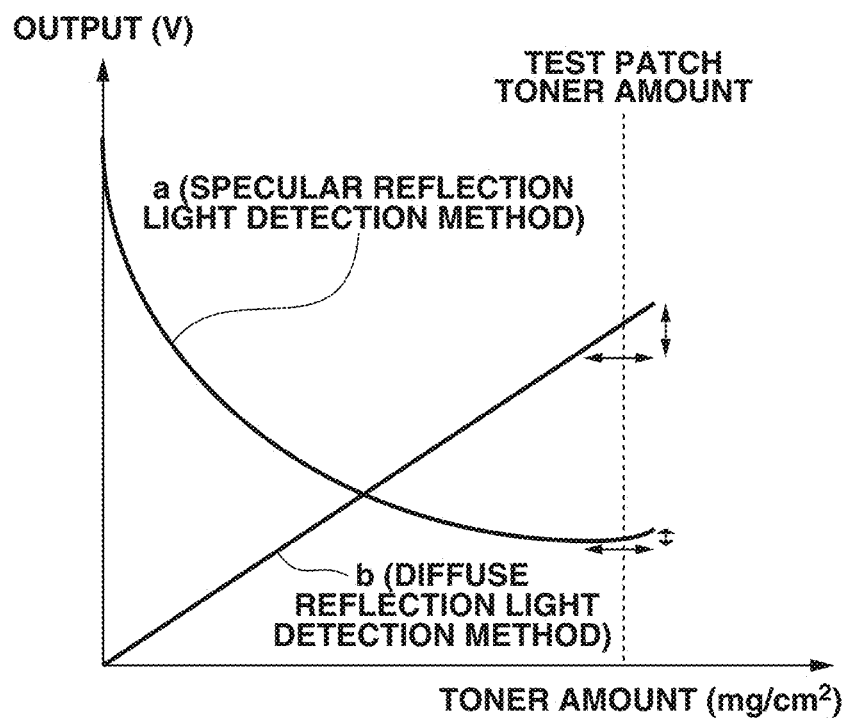
FIG. 7 illustrates a detection output of a light receiving element obtained when a toner amount is varied.

FIG. 6 illustrates a test pattern 400 for density correction control. A plurality of gradation patterns of colors of yellow (401y-405y), magenta (401m-405m), cyan (401c-405c), and black (401k-405k) is formed. FIG. 7 illustrates a detection output of yellow, magenta, and cyan, relative to the toner amount.

A graph (a) illustrated in FIG. 7 indicates the detection result of the light receiving element 63 that receives specular reflection light. Initially, the detection output decreases along with an increase in the toner amount, but the amount of decrease is gradually reduced, and the detection output starts to increase as the toner amount further increases. This stems from the following. That is, although the detection output decreases due to a decrease in the amount of specular reflection light from the intermediate transfer belt 10 in accordance with an increase in the toner amount, the amount of diffuse reflection light from the toner increases, and when the toner amount exceeds a certain amount, the amount of diffuse reflection light exceeds the amount of specular reflection light, which leads to an increase in the detection output. Therefore, the toner amount and the detection output are not in a linear relationship in detection of specular reflection light, and thus optimum density correction cannot be carried out.

A graph (b) illustrated in FIG. 7 indicates the detection result by the light receiving element 62 that receives diffuse reflection light. The detection result increases linearly along with an increase in the toner amount. This is because the amount of diffuse reflection light increases as the toner amount increases. The toner amount and the detection output are in a linear relationship in detection of diffuse reflection light. However, the black toner absorbs most of the infrared light, and the detection output relative to the toner amount is small, which results in a large error when the detection output and the toner amount are put in a linear relationship. Therefore, it is difficult to carry out optimum density correction only by detecting diffuse reflection light.

Accordingly, in the present exemplary embodiment, the density correction is carried out by using the detection result of diffuse reflection light and the detection result of specular reflection light. In other words, the optical sensor 60 outputs, as information relating to the toner density of toner images of a test pattern, a detection output of the light receiving element 62 that corresponds to the detection result of diffuse reflection light and a detection output of the light receiving element 63 that corresponds to the detection result of specular reflection light.

Specifically, the detection output is normalized so that the detection result of specular reflection light and the detection output of diffuse reflection light from a solid toner test patch become equal, and a difference between the specular reflection output and the diffuse reflection output is obtained to thus calculate the net amount of specular reflection light. By carrying out such a calculation, the toner amount and the detection result can be put in a linear relationship through an identical calculation method in all colors of yellow, magenta, cyan, and black, and the density is corrected for each color based on the corresponding result.

The detection result of the test pattern is processed by the DC controller 274. A received light amount signal of the optical sensor 60 is subjected to AD conversion, and the converted signal is output to the DC controller 274. Then, the CPU 276 of the DC controller 274 calculates the net amount of specular reflection light. The image forming conditions are set (modified) based on this calculation result. Specific image forming conditions to be corrected through the density correction control include density factors such as the charging voltage applied to the charging roller 2 (2a, 2b, 2c, 2d), the developing voltage applied to a developing member of the developing device 4 (4a, 4b, 4c, 4d), the light amount of the laser beam from the exposure unit 3 (3a, 3b, 3c, 3d), and the exposure amount corresponding to the density of image data. The setting result of these density factors is stored in the memory 275 of the DC controller 274 and is used during normal image formation or in a subsequent density control.

As described above, the registration correction control and the density control can be carried out by using the optical sensor 60.

[Measures Against Stray Light]

Subsequently, a configuration for measures against stray light in the optical sensor 60 will be described. First, a configuration of a comparative example, in which measures against stray light according to the present exemplary embodiment are not employed, will be described.

Figure 12:
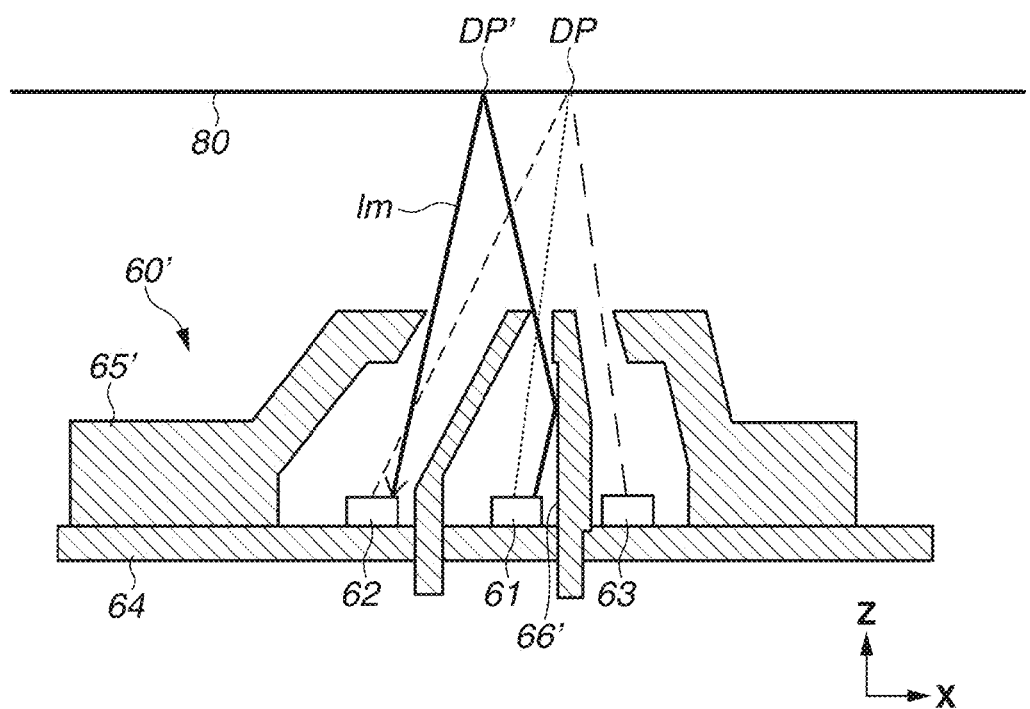
FIG. 12 illustrates a sectional view of an optical sensor and a trajectory of light reflected by an inner wall, according to a comparative example of the first exemplary embodiment.

FIG. 12 is a sectional view of an optical sensor 60' according to the comparative example. In the optical sensor 60' according to the comparative example, components that are different from those in the present exemplary embodiment are given reference numerals followed by "'". Components having reference numerals that are not followed by "'" are similar to the corresponding components in the present exemplary embodiment.

Stray light lm indicates an example of an optical path of light that is emitted from the light emitting element 61 and is specularly-reflected by an inner wall 66' of a housing 65' prior to exiting through the light emitting aperture 71. The light lm specularly-reflected by the inner wall 66' is emitted through the light emitting aperture 71, is specularly-reflected by the surface of the irradiated surface 80 at a position DP' that is different from the detecting position DP, enters through the light receiving aperture 72, and reaches the light receiving element 62. In this manner, not only the diffuse reflection light from the detecting position DP that is to be detected originally but also the stray light lm specularly-reflected at detecting position DP' enters the light receiving element 62 as stray light. Therefore, noise containing a component of specular reflection light reflected at the detecting position DP' may be mixed into the output from the light receiving element 62, and thus an accurate output (a highly precise output) may not be obtained from the light receiving element 62.

Accordingly, in the present exemplary embodiment, the optical sensor 60 is configured so as to suppress a situation in which some (stray light lm) of the light emitted from the light emitting element 61 is specularly-reflected by an inner wall 66 located upstream of the light emitting aperture 71 in the emission direction of light from the light emitting element 61, and the stray light lm then enters the light receiving element 62 after having been specularly-reflected by the irradiated surface 80 at a position different from the detecting position DP. Specifically, the shape of the inner wall 66 of the housing 65 is devised such that stray light is not generated.

Figure 11:
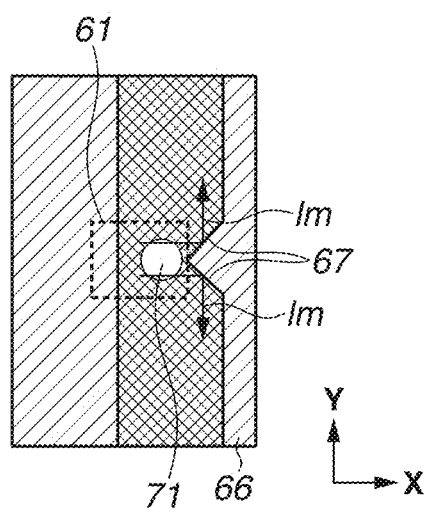
FIG. 11 is a bottom view of the optical sensor according to the first exemplary embodiment, as viewed from the light emitting element.

FIG. 11 is a fragmentary sectional view of the interior of the housing 65 as viewed in the Z direction (refer to FIG. 8) from the side of the light emitting element 61 toward the side of the light emitting aperture 71. The X direction is a direction parallel to the main scanning direction, and a Y direction is a direction orthogonal to the main scanning direction. For convenience, in the Y direction, the direction of the arrow is regarded as a +Y direction and the direction opposite thereto is regarded as a −Y direction. The inner wall 66 of the housing 65 that is on the side opposite to the light receiving element 62 with reference to the light emitting element 61 includes two (a plurality of) slopes 67 formed in such a manner that a section thereof forms a right-angled isosceles shape. In other words, the two slopes 67 intersect with each other orthogonally. The two slopes 67 are inclined relative to the direction (Y direction) that is orthogonal to the direction (X direction) in which the light emitting element 61 and the light receiving element 62 are arrayed, as viewed in the normal direction of the irradiated surface 80. In addition, the two slopes 67 are at different angles relative to the direction (Y direction) that is orthogonal to the direction in which the light emitting element 61 and the light receiving element 62 are arrayed.

Of the light emitted from the light emitting element 61, the stray light lm directed toward the inner wall 66 is specularly-reflected by the two slopes 67. The stray light lm is specularly-reflected by the two slopes 67 and is reflected substantially in the +Y direction or substantially in the −Y direction as illustrated in FIG. 11, and thus the stray light lm does not enter through the light emitting aperture 71. Therefore, a situation in which the stray light lm specularly-reflected by the inner wall 66 enters through the light emitting aperture 71 and is radiated onto the irradiated surface 80 to result in stray light as in the comparative example can be suppressed.

FIGS. 13A and 13B illustrate a comparison between output waveforms obtained when a yellow, magenta, or cyan test patch is detected by the light receiving element 62 in the present exemplary embodiment and in the comparative example. FIG. 13A corresponds to the present exemplary embodiment, and FIG. 13B corresponds to the comparative example. The dynamic range, which is a difference between an output obtained when a toner patch is present on the intermediate transfer belt 10 and an output obtained when a toner patch is not present, is greater in the present exemplary embodiment than in the comparative example. In the case of the comparative example, when a toner patch is not present on the intermediate transfer belt 10, specular reflection light from the inner wall 66' is specularly-reflected by the intermediate transfer belt 10, and reaches the light receiving element 62, and thus the output of the light receiving element 62 greatly increases. In the meantime, when a toner patch is present on the intermediate transfer belt 10, specular reflection light from the inner wall 66' is diffuse-reflected by the toner patch, and most of the diffuse reflection light does not reach the light receiving element 62. Thus, the output of the light receiving element 62 increases only by small amount. In this manner, by forming the slopes 67 as in the present exemplary embodiment, stray light lm entering the light receiving element 62 can be reduced, and a broad dynamic range in the output of the light receiving element 62 can be obtained. Thus, a highly precise output can be obtained. Therefore, the detection precision of the test patch on the intermediate transfer belt 10 is stabilized.

In addition, the configuration of the slopes 67 is not limited to the configuration described above. In other words, the number of the slopes 67 and the orientation (angle) of each slope 67 are not limited as long as the slope 67 has such a shape that the stray light lm emitted from the light emitting element 61 and entering the slope 67 does not enter through the light receiving aperture 72 corresponding to the light receiving element 62 after having been specularly-reflected by the slope 67. In other words, the slope 67 may have any shape as long as the stray light lm emitted from the light emitting element 61 and entering the slope 67 does not enter through the light emitting aperture 71 after having been reflected by the slope 67 or does not enter through the light receiving aperture 72 even if the stray light lm enters through the light emitting aperture 71 and is specularly-reflected by the irradiated surface 80.

Figure 14A:
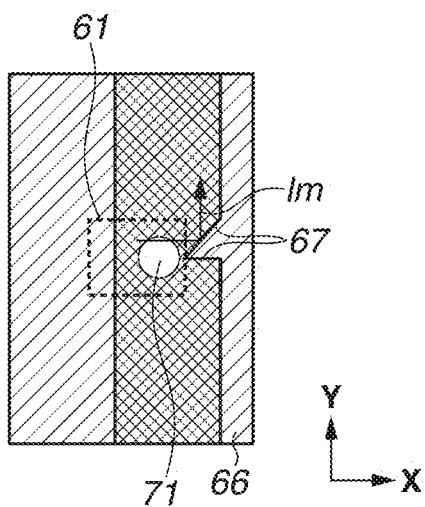
FIGS. 14A, 14B, and 14C are bottom views of optical sensors having other configurations according to the first exemplary embodiment.
Figure 14B:
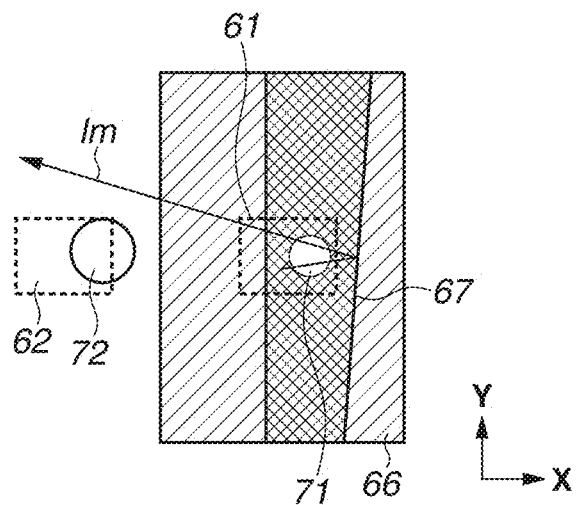
Figure 14C:
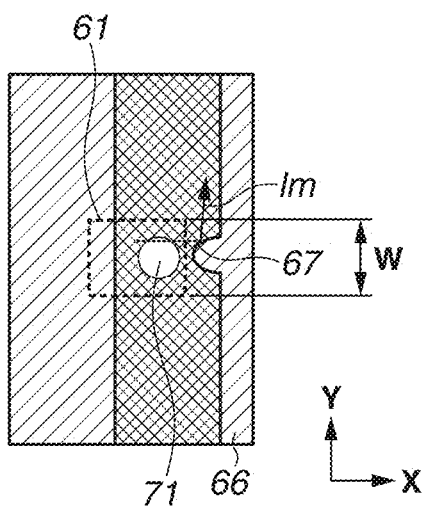

FIGS. 14A, 14B, and 14C are sectional views, as viewed in the Z direction as in FIG. 11, illustrating other configurations. As another configuration, for example, as illustrated in the sectional view as viewed in the Z direction in FIG. 14A, two slopes 67 may be configured to intersect with each other at an angle of 45°. Alternatively, as illustrated in the sectional view as viewed in the Z direction in FIG. 14B, only a single slope 67 may be provided. As yet another configuration, as illustrated in FIG. 14C, an arc-shaped surface having an arc-shaped section may be provided. In this case, the arc-shaped surface corresponds to the slope 67.

It is sufficient that the slope 67 is present at least at a position of the inner wall 66 that overlaps a portion corresponding to a width W (refer to FIG. 14C) of the light emitting element 61 in the Y direction. In other words, it is sufficient that the slope 67 is present at least at a portion of the inner wall 66 that faces a portion of the light emitting element 61 that corresponds to the width W, in the X direction.

In addition, it is sufficient that the slope 67 has such a shape that the stray light lm that has been emitted from the light emitting element 61 and is specularly-reflected by the slope 67 does not enter through the light receiving aperture 72 corresponding to the light receiving element 62. It is more desirable, however, that the slope 67 have such a shape that the stray light lm does not enter through the light emitting aperture 71 after having been specularly-reflected by the slope 67. With such a configuration, a situation in which the stray light lm enters the light receiving element 62 can be suppressed more reliably.

In addition, as illustrated in FIGS. 11, 14A, and 14C, by providing the inner wall 66 with a protruding portion having a cross-section shape protruding toward the light emitting element 62, and by the surface of the protruding portion functioning as the slope 67, occurrence of stray light lm can be suppressed more effectively.

In addition, a configuration in which the optical sensor 60 includes, as light receiving elements, the light receiving element 62 that receives diffuse reflection light and the light receiving element 63 that receives specular reflection light has been described in the present exemplary embodiment. The configuration of the optical sensor 60, however, is not limited to such a configuration. In other words, the optical sensor 60 does not necessarily include the light receiving element 63 that receives specular reflection light and may be formed by the light emitting element 61 and the light receiving element 62 that receives diffuse reflection light, in a case in which an output from the optical sensor 60 is not used in the density control. In the optical sensor 60 configured in this manner as well, the configuration in which the slope 67 is provided as described above can be applied.

In addition, aside from providing the slope 67, anti-reflection processing may be applied to the inner wall 66 by, for example, providing fine protrusions and recesses for reducing reflection.

As described thus far, according to the present exemplary embodiment, a situation in which the light lm specularly-reflected by the inner wall 66 reaches the light receiving element 62 as stray light lm can be suppressed by providing the slope 67 on the inner wall 66 of the housing 65 that encloses the light emitting element 61. As a result, an accurate output (a highly precise output) can be obtained from the light receiving element 62. In addition, the dynamic range, which is a difference between an output of the light receiving element 62 obtained when a test patch is detected and an output of the light receiving element 62 obtained when the surface of the intermediate transfer belt 10 is detected, is broadened, and thus the detection precision of the test patch can also be improved.

Figure 15A:
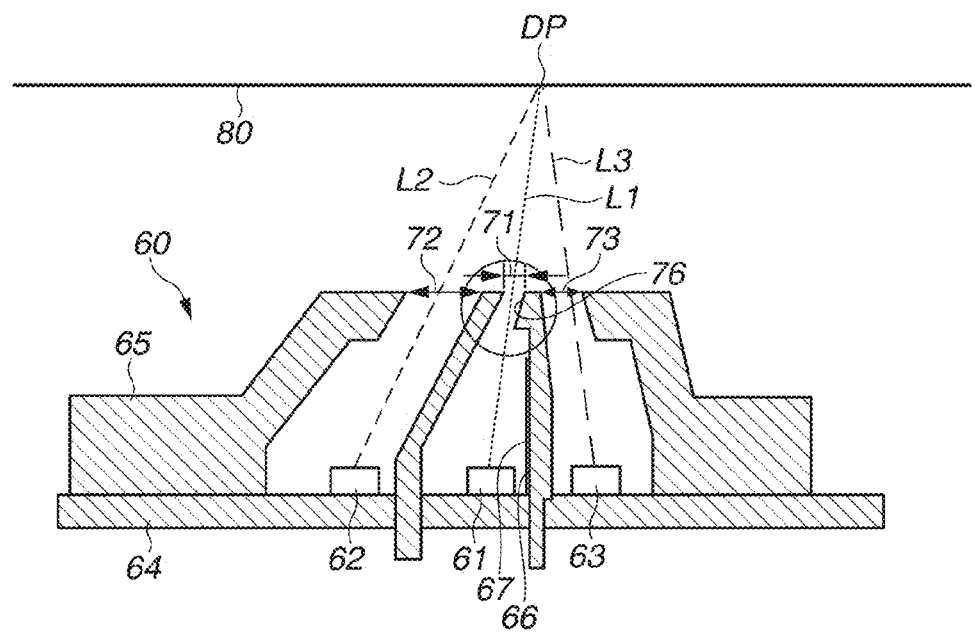
FIGS. 15A and 15B are sectional views of an optical sensor according to a second exemplary embodiment.
Figure 15B:
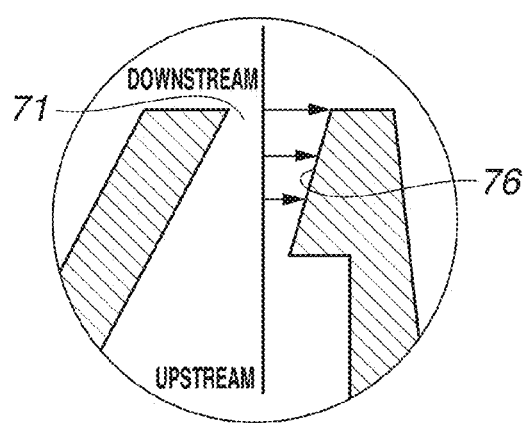
Figure 16A:
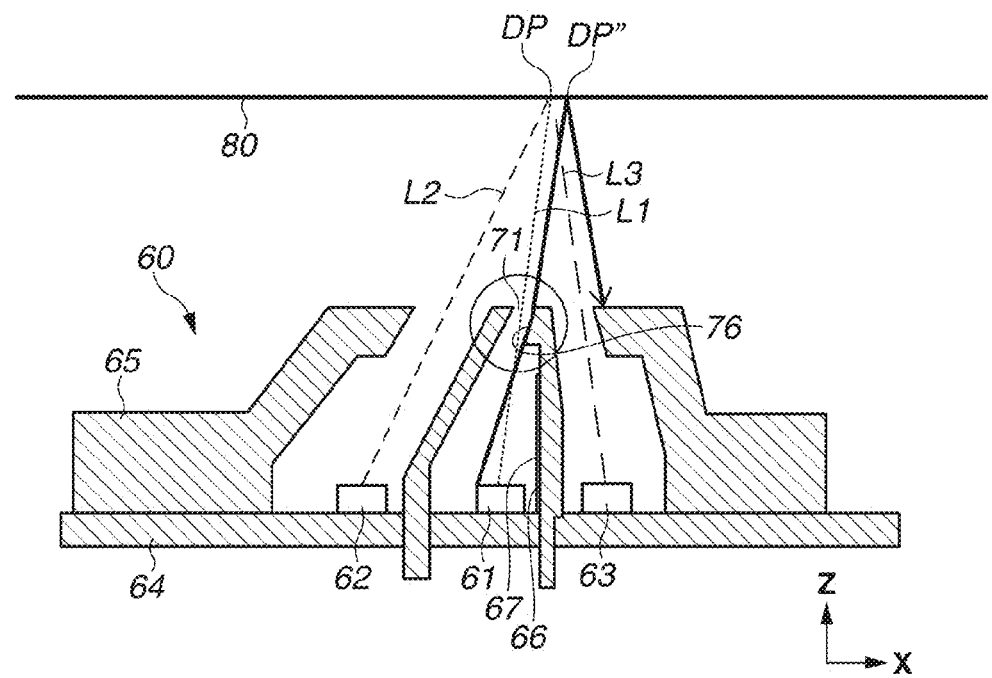
FIGS. 16A and 16B illustrate a trajectory of light reflected by an aperture of the optical sensor according to the second exemplary embodiment.
Figure 16B:
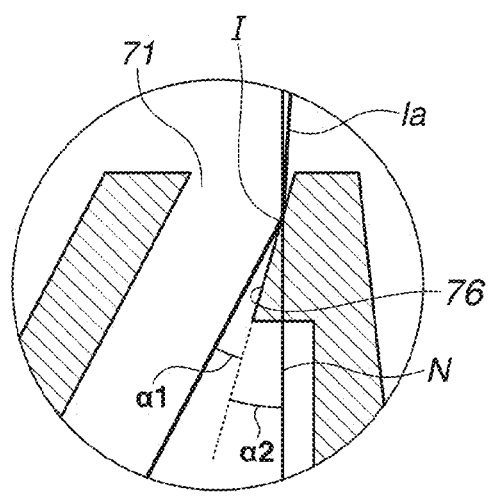

Subsequently, a second exemplary embodiment will be described. Configurations similar to those of the first exemplary embodiment are given identical reference numerals, and descriptions thereof will be omitted. In the present exemplary embodiment, a configuration for suppressing stray light generated in a path different from that of the first exemplary embodiment will be described. FIG. 15A is a sectional view of an optical sensor 60 as viewed in a direction parallel to the surface of the irradiated surface 80. FIG. 15B is a fragmentary enlarged view of the light emitting aperture 71 illustrated in FIG. 15A and the vicinity thereof. In the present exemplary embodiment, in the inner surface of the light emitting aperture 71, an inner surface 76 located on the side of the light receiving element 63 is inclined toward a side opposite to the light receiving element 62 from the upstream to the downstream in the emission direction of light from the light emitting element 61. Subsequently, the trajectory of a light ray that reaches the inner surface 76 of the light emitting aperture 71 will be described. FIG. 16A is a sectional view of the optical sensor 60 as viewed in a direction parallel to the surface of irradiated surface 80, and illustrates an example of the trajectory of the light specularly-reflected by the inner surface 76 of the light emitting aperture 71. FIG. 16B is a fragmentary enlarged view of the light emitting aperture 71 illustrated in FIG. 16A and the vicinity thereof. Light la, which is part of infrared light radiated from the light emitting element 61, may be specularly-reflected by the inner surface 76 of the light emitting aperture 71 and may reach the irradiated surface 80, due to a variation in the mounting position of the light emitting element 61. Even in such a case, in the present exemplary embodiment, the optical sensor 60 is configured such that the light la does not reach the light receiving element 62 even when the light la specularly-reflected by the inner surface 76 of the light emitting aperture 71 is further specularly-reflected by the irradiated surface 80.

Specifically, as illustrated in FIG. 16B, an angle $\alpha 1$ indicates an angle at which the light la enters the inner surface 76, and angle $\alpha 2$ indicates an angle formed between the slope of the inner surface 76 and the normal N of the irradiated surface 80. The light la that has entered the inner surface 76 of the light emitting aperture 71 at the angle $\alpha 1$ is specularly-reflected by the inner surface 76 at the angle $\alpha 1$ relative to the inner surface 76. Here, when the angle relationship satisfies $\alpha 1 < \alpha 2$, the light la that has been specularly-reflected by the inner surface 76 is not specularly-reflected toward the side of the light receiving element 62 with reference to the normal N of the irradiated surface 80 that passes through an incident point I at which the light la enters the inner surface 76. Therefore, even when the light la that has been specularly-reflected by the inner surface 76 at a detecting position DP" is specularly-reflected by the irradiated surface 80, the light la does not reach the light receiving element 62.

In addition, anti-reflection processing may be applied to the inner wall 76 by, for example, providing fine protrusions and recesses for reducing reflection.

As described thus far, by inclining the inner surface 76 toward the side opposite to the light receiving element 62 from the upstream to the downstream in the emission direction of the light from the light emitting element 61, stray light can be controlled so as not to enter the light receiving element 62, and an accurate output (a highly precise output) can be obtained from the light receiving element 62. In addition, the dynamic range, which is a difference between an output of the light receiving element 62 obtained when a test patch is detected and an output of the light receiving element 62 obtained when the surface of the intermediate transfer belt 10 is detected, is broadened, and thus the detection accuracy of the test patch can also be improved.

Figure 17:
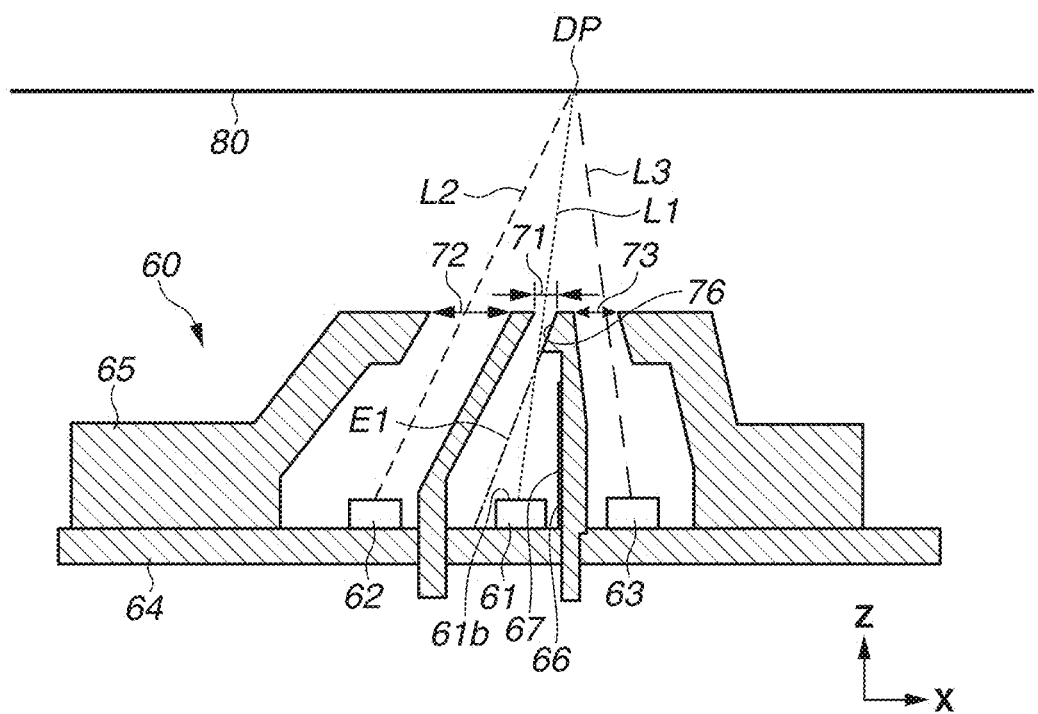
FIG. 17 is a sectional view illustrating a more desirable optical sensor according to the second exemplary embodiment.

In addition, as another configuration of the second exemplary embodiment, a configuration for more reliably suppressing a situation in which light specularly-reflected by the inner surface 76 of the light emitting aperture 71 results in stray light will be described. In order to more reliably suppress a situation in which light specularly-reflected by the inner surface 76 of the light emitting aperture 71 results in stray light, it is effective to prevent light from directly entering the inner surface 76 from the light emitting element 61. A situation in which the light directly enters the inner surface 76 corresponds to a situation in which the light emitted from the light emitting element 61 enters the inner surface 76 without being reflected by a portion of the housing 65 other than the inner surface 76 or by the substrate 64. Conditions for achieving the above will be described. FIG. 17 is a sectional view illustrating an optical sensor 60 having another configuration, as viewed in a direction parallel to the surface of the irradiated surface 80. In order to prevent the light from directly entering the inner surface 76 from the light emitting element 61, it is sufficient that at least a light emitting point 61b of the light emitting element 61 is disposed closer to the side of the substrate 64 than an auxiliary line E1 extending from the inner surface 76. With such a configuration, light does not directly enter the inner surface 76 from the light emitting element 61. Therefore, stray light can be controlled so as not to enter the light receiving element 62, and an accurate output (a highly precise output) can be obtained from the light receiving element 62. In addition, the dynamic range, which is a difference between an output of the light receiving element 62 obtained when a test patch is detected and an output of the light receiving element 62 obtained when the surface of the intermediate transfer belt 10 is detected, is broadened, and thus the detection accuracy of the test patch can also be improved.

Figure 18A:
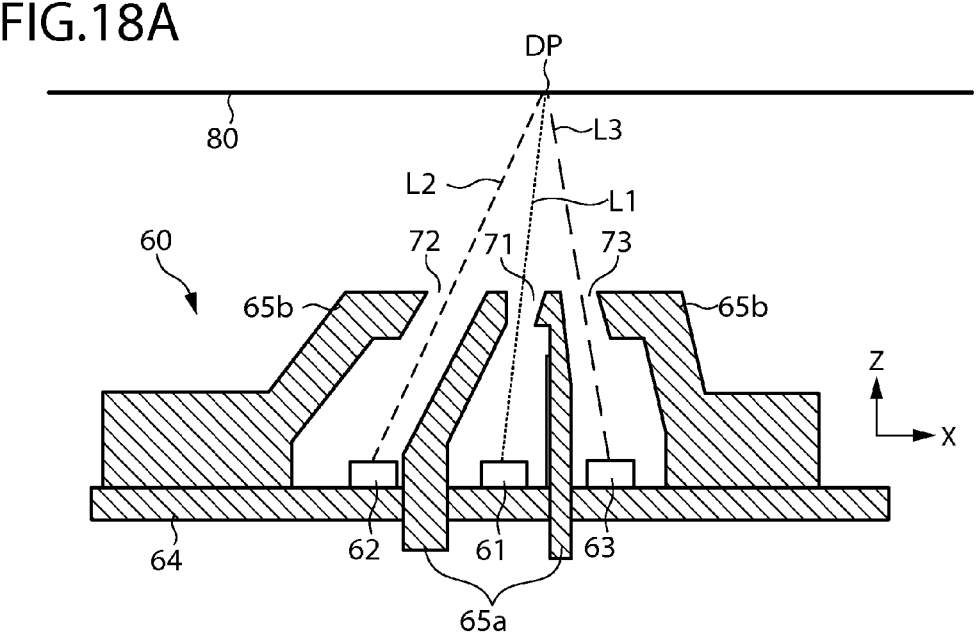
FIG. 18A is a sectional view illustrating an optical sensor having another configuration according to the second exemplary embodiment.

In addition, when mass productivity of the housing 65 is considered, as illustrated in the sectional view illustrated in FIG. 18A, the housing 65 may have a two-body structure formed by a first housing member 65a and a second housing member 65b. FIG. 18A is a sectional view of the optical sensor 60 as viewed in a direction parallel to the surface of the irradiated surface 80. As illustrated in FIG. 18A, the first housing member 65a encloses the light emitting element 61 in a space thereinside (space defined by the first housing member 65a and the substrate 64), and the light emitting aperture 71 and portions of the light receiving apertures 72 and 73 that are to be disposed toward the side of the light emitting aperture 71 are formed in the first housing member 65a. The second housing member 65b encloses the light receiving elements 62 and 63 disposed outside the first housing member 65a in spaces thereinside (spaces defined by the second housing member 65b, the first housing member 65a, and the substrate 64). Portions of the light receiving apertures 72 and 73 that are to be disposed toward the side opposite to the light emitting aperture 71 are formed in the second housing member 65b. The first housing member 65a and the second housing member 65b engage with each other through an engagement unit (not illustrated) and are thus positioned relative to each other, forming a single housing 65. By forming the housing 65 by two separate members in this manner, the molding precision and the production efficiency of the housing 65 can be improved.

Figure 18B:
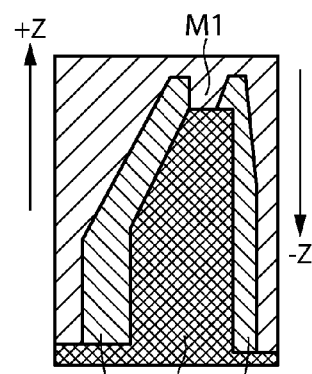
FIGS. 18B and 18C are schematic diagrams for describing how a housing is removed from a mold.
Figure 18C:
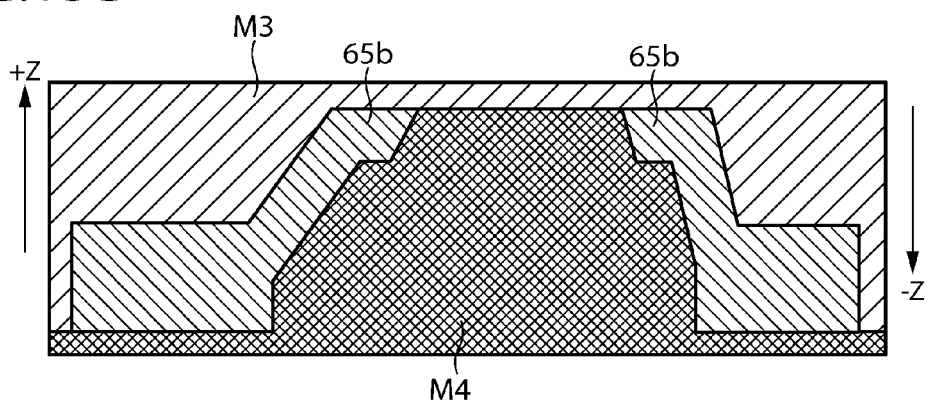

FIG. 18B is a sectional view illustrating how the first housing member 65a is resin-molded. FIG. 18C is a sectional view illustrating how the second housing member 65b is resin-molded. The first housing member 65a and the second housing member 65b are resin-molded members. The first housing member 65a is molded in molds M1 and M2 illustrated in FIG. 18B. Concerning the molding method, in a state in which the mold M1 and the mold M2 are closed, a molding material (resin) is poured into a space between the two molds M1 and M2. Subsequently, after the molding material is cooled, the mold M1 is pulled in the +Z direction, and the mold M2 is pulled in the −Z direction. Thus, the first housing member 65a is released from the molds M1 and M2. In addition, the second housing member 65b is molded in molds M3 and M4 illustrated in FIG. 18C. Concerning the molding method, in a state in which the mold M3 and the mold M4 are closed, a molding material (resin) is poured into a space between the two molds M3 and M4. Subsequently, after the molding material is cooled, the mold M3 is pulled in the +Z direction, and the mold M4 is pulled in the −Z direction. Thus, the second housing member 65b is released from the molds M3 and M4.

In this manner, by forming the housing 65 by two separate members (the first housing member 65a and the second housing member 65b), each of the members can be fabricated through simple molding. Therefore, even if the housing 65 has a complicated shape so as to enclose a plurality of light emitting elements and light receiving elements, the housing 65 can be fabricated at low cost and with high molding precision.

The optical sensor 60 described in the second exemplary embodiment may include the slope 67 described in the first exemplary embodiment.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-014192 filed Jan. 29, 2014, which is hereby incorporated by reference herein in its entirety.

What is claimed is:

1. An optical detection device, comprising:
   a light emitting element being positioned by being mounted on a substrate;
   a light receiving element;
   a housing including a first aperture through which light emitted from the light emitting element passes and a second aperture which is different from the first aperture and through which light to be received by the light receiving element passes, and enclosing the light emitting element and the light receiving element, wherein light emitted from the light emitting element reaches the light receiving element through the second aperture after passing through the first aperture and being reflected by an irradiated surface; and
   a slope provided in the housing and inclined in a direction orthogonal to an array direction of the light emitting element and the light receiving element, as viewed in a normal direction of the irradiated surface, wherein the slope is provided at a portion on an upstream side of the first aperture in an emission direction of light from the light emitting element, the slope faces the light emitting element in the array direction, and light emitted from the light emitting element enters the slope.

2. The optical detection device according to claim 1, wherein the housing includes a plurality of the slopes, and the plurality of slopes has different angles from each other relative to the direction orthogonal to the array direction.

3. The optical detection device according to claim 2, wherein the housing includes a protruding portion protruding toward the light emitting element, and the slope is a surface of the protruding portion.

4. The optical detection device according to claim 3, wherein the surface of the protruding portion is an arc-shaped surface.

5. The optical detection device according to claim 1, wherein the slope is provided at a portion of the housing that faces the light emitting element in the array direction.

6. The optical detection device according to claim 5, wherein the light receiving element is mounted on the substrate.

7. The optical detection device according to claim 6, wherein the light receiving element receives light diffuse-reflected at a predetermined position of the irradiated surface.

8. The optical detection device according to claim 7, wherein light emitted from the light emitting element and specularly-reflected by the slope does not enter through the first aperture, or does not enter through the second aperture after passing through the first aperture and being specularly-reflected by the irradiated surface.

9. The optical detection device according to claim 8, wherein an inner surface of the first aperture of the housing is inclined toward a side opposite to the light receiving element from an upstream to a downstream in an emission direction of light from the light emitting element.

10. The optical detection device according to claim 9, wherein light emitted from the light emitting element does not directly enter the inner surface of the first aperture.

11. The optical detection device according to claim 10, wherein the housing includes a first housing member and a second housing member, and the light emitting element is enclosed in a space inside the first housing member and the light receiving element is enclosed in a space that is outside the first housing member and is inside the second housing member.

12. An image forming apparatus for forming an image on a recording material by transferring a toner image onto the recording material, the image forming apparatus comprising:
   an image forming unit configured to form a toner image on an image bearing member;
   an optical detection device including:
      a light emitting element being positioned by being mounted on a substrate;
      a light receiving element;
      a housing including a first aperture through which light emitted from the light emitting element passes and a second aperture which is different from the first aperture and through which light to be received by the light receiving element passes, and enclosing the light emitting element and the light receiving element, wherein light emitted from the light emitting element reaches the light receiving element through the second aperture after passing through the first aperture and being reflected by an irradiated surface of the image bearing member; and a slope provided in the housing and inclined a direction orthogonal to in an array direction of the light emitting element and the light receiving element, as viewed in a normal direction of the irradiated surface, wherein the slope is provided at a portion on an upstream side of the first aperture in an emission direction of light from the light emitting element, the slope faces the light emitting element in the array direction, and light emitted from the light emitting element enters the slope; and a control unit configured to control an image forming condition of the image forming unit based on an output from the optical detection device.

13. The image forming apparatus according to claim 12, wherein the housing includes a plurality of the slopes, and the plurality of slopes has different angles from each other relative to the direction orthogonal to the array direction.

14. The image forming apparatus according to claim 13, wherein the housing includes a protruding portion protruding toward the light emitting element, and the slope is a surface of the protruding portion.

15. The image forming apparatus according to claim 14, wherein the surface of the protruding portion is an arc-shaped surface.

16. The image forming apparatus according to claim 12, wherein the slope is provided at a portion of the housing that faces the light emitting element in the array direction.

17. The image forming apparatus according to claim 16, wherein the light receiving element is mounted on the substrate.

18. The image forming apparatus according to claim 17, wherein the light receiving element receives light diffuse-reflected at a predetermined position of the irradiated surface.

19. The image forming apparatus according to claim 18, wherein light emitted from the light emitting element and specularly-reflected by the slope does not enter through the first aperture or does not enter through the second aperture after passing through the first aperture and being specularly-reflected by the irradiated surface.

20. The image forming apparatus according to claim 19, wherein an inner surface of the first aperture of the housing is inclined toward a side opposite to the light receiving element from an upstream to a downstream in an emission direction of light from the light emitting element.

21. The image forming apparatus according to claim 20, wherein light emitted from the light emitting element does not directly enter the inner surface of the first aperture.

22. The image forming apparatus according to claim 21, wherein the housing includes a first housing member and a second housing member, and the light emitting element is enclosed in a space inside the first housing member and the light receiving element is enclosed in a space that is outside the first housing member and is inside the second housing member.

23. The image forming apparatus according to claim 12, wherein the control unit controls an image forming condition based on a timing of an output from the optical detection device.

24. The image forming apparatus according to claim 12, wherein the optical detection device outputs information relating to toner density of a toner image borne on the image bearing member.

* * * * *